(12) United States Patent
Jakoby (10) Patent No.: US 7,694,551 B2
(45) Date of Patent: Apr. 13, 2010

(54) SENSOR

(75) Inventor: Bernhard Jakoby, Linz (AT)

(73) Assignee: Robert Bosch GmbH, Stuttgart (DE)

(*) Notice: Subject to any disclaimer, the term of this patent is extended or adjusted under 35 U.S.C. 154(b) by 378 days.

(21) Appl. No.: 10/581,006

(22) PCT Filed: Nov. 22, 2004

(86) PCT No.: PCT/AT2004/000409

§ 371 (c)(1),
(2), (4) Date: Mar. 16, 2007

(87) PCT Pub. No.: WO2005/052554

PCT Pub. Date: Jun. 9, 2005

(65) Prior Publication Data
US 2007/0272002 A1    Nov. 29, 2007

(30) Foreign Application Priority Data
Nov. 26, 2003 (AT) .............................. A 1895/2003
Oct. 11, 2004 (AT) .............................. A 1688/2004

(51) Int. Cl.
*G01N 11/10* (2006.01)
(52) U.S. Cl. .................................................. 73/54.26
(58) Field of Classification Search ............... 73/54.26, 73/54.01, 54.24, 54.23, 54.28
See application file for complete search history.

(56) References Cited

U.S. PATENT DOCUMENTS

| | | | | |
|---|---|---|---|---|
| 5,394,739 A | * | 3/1995 | Garvey et al. ............... | 73/54.23 |
| 5,958,269 A | * | 9/1999 | Suzuki et al. ............... | 219/216 |
| 6,939,451 B2 | * | 9/2005 | Zhao et al. .................. | 204/451 |
| 6,961,516 B2 | * | 11/2005 | Toya et al. .................. | 392/397 |

(Continued)

FOREIGN PATENT DOCUMENTS

| | | |
|---|---|---|
| DE | 196 44 290 | 5/1998 |
| DE | 199 32 601 | 1/2001 |
| EP | 0 714 022 | 5/1996 |
| EP | 0 897 216 | 2/1999 |

OTHER PUBLICATIONS

S. J. Marlin, G. C. Frye, K. O. Wessendorf: "Sensing Liquid Properties with Thickness-Shear Mode Resonators," Sens. Act. A, vol. 44, pp. 209-218, 1994.

(Continued)

*Primary Examiner*—John Fitzgerald
(74) *Attorney, Agent, or Firm*—Kenyon & Kenyon LLP (57) ABSTRACT

A sensor for measuring a liquid viscosity includes at least one piezo-electrical element in the form of a resonator, at least one first exciting electrode, and a second exciting electrode. At least the first exciting electrode is arranged on the sensitive surface of the sensor and, in order to reduce measuring time at predefined temperatures, the sensor is provided with a heating electrode for heating a measurable liquid.

13 Claims, 8 Drawing Sheets

U.S. PATENT DOCUMENTS

| | | | |
|---|---|---|---|
| 7,043,969 B2 * | 5/2006 | Matsiev et al. | 73/54.41 |
| 7,257,984 B2 * | 8/2007 | Pidria et al. | 73/10 |
| 2002/0170341 A1 | 11/2002 | Jakoby et al. | |
| 2002/0194906 A1 * | 12/2002 | Goodwin et al. | 73/152.46 |
| 2003/0051534 A1 * | 3/2003 | Niwa et al. | 73/54.01 |
| 2005/0145019 A1 * | 7/2005 | Matsiev et al. | 73/53.01 |
| 2006/0010964 A1 * | 1/2006 | Sparks et al. | 73/54.01 |

OTHER PUBLICATIONS

B. Jakoby, M. J. Vellekoop, "Properties of Love Waves: Applications in Sensors," Smart Mater. Struct., vol. 6, pp. 668-679, 1997.

B. Jakoby and M. J. Vellekoop, "Analysis and Optimization of Love Wave Liquid Sensors," IEEE Trans. on Ultrason., Ferroelec., and Freq. Contr., vol. 45, pp. 1293-1302, Sep. 1998.

* cited by examiner

SENSOR

FIELD OF THE INVENTION

The present invention relates to a sensor for measuring the viscosity of a liquid, including at least one piezoelectric component, e.g., a resonator, and at least one first starting electrode and one second starting electrode, at least the first starting electrode being situated on a sensitive surface of the sensor.

BACKGROUND INFORMATION

Viscosity measurement using microacoustic components is known in the art. In these components, mechanical or acoustic oscillations can be induced in a piezoelectric element by applying alternating electric voltages to electrode configurations situated on the same piezoelectric element. In general, piezoelectric crystals (such as quartz), but also piezoelectric ceramics, are used as piezoelectric materials. In the case of crystals, it is possible to induce preferably shear oscillations on at least one crystal surface via an appropriate selection of the used crystal orientation (known as crystal section) during excitation with an alternating voltage at appropriately applied electrodes. In the case of piezoelectric ceramics, the direction of polarization is to be selected in a similar manner. The term "shear oscillation" describes oscillating deformations of the surface formed preferably in the plane of the crystal surface (i.e., not perpendicularly to the surface). If a crystal surface oscillating in this way is brought into contact with a viscous liquid, a damped acoustic shear wave is induced in the liquid. If the acoustic component is designed as a piezoelectric resonator, the damping and the resonance frequency of the resonator will change due to this contact with the liquid as a function of the density and viscosity of the liquid (see, for example, S. J. Marlin, G. C. Frye, K. O. Wessendorf; "Sensing Liquid Properties with Thickness-Shear Mode Resonators," Sens. Act. A, vol. 44. p. 209-218, 1994). These two changes result in corresponding changes in the electrical parameters of the electric equivalent circuit for the resonator impedance, which may be detected using suitable electronic analyzer circuits. The viscosity of the liquid may thus be electronically measured.

Microacoustic components using shear-polarized acoustic surface waves are based on a similar principle (see, for example, B. Jakoby, M. J. Vellekoop, "Properties of Love Waves: Applications in Sensors," Smart Mater. Struct, vol. 6, p. 668-679, 1997). Also in this case, shear waves which modify the electrical properties of the component are induced in the liquid. These components may also be designed as resonators, but alternatively also as delay lines. In this case the damping and the propagation time, i.e., phase of the delay line, change with the viscosity and density of the liquid.

Published U.S. patent application US 2002/0170341 A1 (Jakoby et al.) describes a measuring system for the viscosity measurement of liquids. Based on the problem that in measuring the viscosity of aggressive or corrosive liquids the sensitive surfaces of the sensors used are sealed using gaskets and the stress by the gaskets affecting the measurements, published U.S. patent application US 2002/0170341 A1 describes a piezoelectric sensor device which is completely immersed in the liquid to be measured. A cylinder-shaped sensor having two starting electrodes is described, the sensor being situated in a container through which the liquid to be measured flows.

Since the viscosity of a liquid generally varies considerably with the temperature, typically viscosity-temperature (VT) characteristics are measured. This requires an additional unit for exact temperature control of the liquid, which often substantially increases the required space and the price of the overall measuring device. As a further disadvantage, many liquids have a high specific heat, resulting in a relatively long heating time depending on the size of the required sample volume.

SUMMARY

An object of the present invention is to provide a sensor which avoids the above-mentioned disadvantages and which shortens the time for measuring the viscosity of a liquid at a predefinable temperature, and which has a simple and compact design, and which is inexpensive to manufacture and use.

This is achieved according to the present invention by providing at least one heating electrode for heating the liquid to be measured.

The liquid to be measured may thus be heated to a predefinable temperature in the area of the sensor. Since the liquid is heated directly in the area of the sensor, the entire measuring structure is compact and inexpensive. Since the liquid is heated in the area of the sensor, the predefinable temperature is quickly attained, which considerably shortens the total measuring time.

Compared to conventional viscosity measurements, microacoustic measurement has the advantage that only relatively small amounts of sample are needed, since the penetration depth of the damped shear wave into the liquid is relatively small (typically on the order of a few micrometers), so that covering the sensor with a thin liquid film is sufficient in principle; in addition, the component may generally have a very compact design, typically on the order of a few millimeters.

In an example embodiment of the present invention, the at least one heating electrode may be situated on or next to the sensitive surface of the sensor. This ensures that the part of the liquid directly affected by the measurement is heated, and not other parts of the liquid which are unimportant for the measurement.

In this context, the at least one heating electrode may be designed in one piece with the first starting electrode. An additional electrode is thus not necessary, and it is ensured that the liquid is heated next to the measuring point. This saves additional measuring time.

According to another example embodiment of the present invention, the at least one heating electrode may span a surface area having a central area, e.g., a center, in particular a center point, and may have an approximately uniform temperature distribution over the surface area in the operating temperature range. A uniform temperature of the liquid to be measured may ensure that the measured viscosity is also the actual viscosity of the liquid at this temperature.

In an example embodiment of the present invention, the at least one heating electrode may have a meandering shape. This allows the surface area to be heated to be configured in a simple manner according to the requirements for temperature distribution over the surface area.

In another example embodiment of the present invention, the at least one heating electrode may have at least two areas of different resistance per unit of length. This allows at least one area to be heated more or less intensively than another area. This allows a predefinable temperature distribution over the surface area to be achieved.

In another example embodiment of the present invention, the at least one heating electrode may have at least two areas of different cross section. This makes it possible in a simple manner for a heating electrode entirely manufactured from a single material to have areas of different resistance per unit of length.

In a variant of the present invention, the resistance per unit of length of the at least one heating electrode may vary as a function of its distance from the central area, e.g., from the center, in particular from the center point. This allows the usually prevailing temperature distribution of heated surface areas, having a substantially higher temperature in the middle of the heated surface area, to be equalized for a largely homogeneous temperature distribution, since the resistance per unit of length determines the temperature rise of the heating electrode.

In another variant of the present invention, the resistance per unit of length of the at least one heating electrode may increase from the central area, e.g., from the center, in particular from the center point, toward an edge area. This causes the edge to be more intensively heated than the center of the surface area, which causes a more homogeneous temperature distribution to be established over the surface area than in the case of uniform heating of the surface area. When viscosity is measured using a microacoustic component, the acoustic waves only very slightly penetrate the liquid to be measured. Therefore, and because of the rather low thermal conductivity of most liquids, it may be assumed that the temperature distribution in the liquid directly above the heated surface area and in the area of the penetration depth of the acoustic waves is the same as the temperature distribution of the heated surface area.

In an example embodiment of the present invention, a temperature measuring sensor may be provided. This allows the actual temperature prevailing in the liquid to be determined by the sensor.

In another example embodiment, the temperature measuring sensor may include the at least one heating electrode. The heating electrode, which is present anyway, may thus also be used for temperature measurement, making a separate component unnecessary.

According to another example embodiment of the present invention, at least one of the starting electrodes and/or the at least one heating electrode may be coated with an insulation layer. This allows the liquid to be electrically, i.e., galvanically, isolated from the electrode(s). This is recommended in particular in the case of electrically conductive liquids. Furthermore, a non-conductive liquid represents a dielectric material, whose capacitive interactions with the starting electrodes operated using alternating voltage may affect the measurements.

The present invention further provides a device for measuring the viscosity of liquids, in which device a sensor according to the present invention is provided. This allows all the above-mentioned advantages of a sensor of this type to be transferred to a device for measuring the viscosity of liquids.

The present invention further provides a method for measuring the viscosity of liquids, in which at least one sensitive surface of a sensor is brought into contact with the liquid to be measured, the sensor is induced to oscillate by applying an alternating voltage, and a viscosity value of the liquid is ascertained from measured values of the electrical parameters, preferably voltage and current.

In the known methods for viscosity measurement in liquids, the viscosity is typically ascertained as a function of the liquid's temperature. In this case the liquid must be heated to the measuring temperature. Since most liquids have a relatively high specific heat, this requires a relatively long heating time between the individual measurements. Such a measurement procedure is therefore very time-consuming. In addition, considerable amounts of the liquid to be measured are needed.

The present invention avoids the above-named disadvantages and makes measurements in a substantially reduced time possible.

This is achieved according to the present invention by heating the liquid with the aid of a heating electrode in the area of the sensitive surface.

In this way, only the part of the liquid which is relevant for the measurement is heated. This takes place in a relatively short time and requires considerably less energy than heating a large amount of liquid. In addition, in a method of this type for viscosity measurement in liquids, only a small amount of liquid is needed for performing the method. It may thus be sufficient to wet the sensitive and heated surface of the sensor with the liquid to be measured.

In accordance with the present invention, the temperature of the liquid may be measured. This makes temperature values which are important as a reference for the measurement also available.

In one example implementation of the method of the present invention, upon reaching a predefinable temperature, the heating of the liquid may be interrupted, the electrical parameters may be measured, and the viscosity value of the liquid may be ascertained. In this way, no further heating takes place during the measurement. Due to its high specific heat, the liquid does not noticeably or measurably cool off during the short measuring phase. This also allows additional polarization of the piezoelectric component to be prevented.

According to another embodiment of the present invention, the viscosity values of the liquid may be ascertained for a plurality of predefinable temperatures. This allows conclusions to be drawn regarding the viscosity of a liquid at different predefinable temperatures.

In this context, a curve of the liquid's viscosity plotted against temperature may be formed from the individual viscosity values of the liquid at the predefinable temperatures. This allows intermediate viscosity values to be interpolated from the ascertained viscosity values of the liquid.

DETAILED DESCRIPTION

FIGS. 1 through 5 show two example embodiments of sensors S according to the present invention for measuring the viscosity of a liquid, including at least one piezoelectric component 1 designed as a resonator and at least one first starting electrode 7 and one second starting electrode 3, at least the first starting electrode 7 being situated on a sensitive surface 8 of sensor S, and at least one heating electrode 2 being provided for heating the liquid to be measured.

In the figures, the visible surfaces of first starting electrode 7, of second starting electrode 3, and of heating electrode 2 are shown with crosshatching for better contrast of electrodes 2, 3, 7 against their surroundings.

Sensor S according to the present invention may be manufactured using cost-effective microtechnological processes. Compared with conventional viscosimeters and sensors used therein, a sensor S according to the present invention may be manufactured comparatively advantageously in large numbers and, due to its measuring principle, needs only a small amount of sample. Due to heating electrode 2 integrated according to the present invention and due to integrated temperature measuring sensor 26, the liquid layer which is relevant for the measurement may be heated rapidly and in a controlled manner at sensitive surface 8, which results in a shorter overall measuring time compared with conventional methods. Therefore, the entire system requires a substantially lower heating power than conventional devices.

Liquid is understood as a fluid in the present application. The viscosity of substances that are solid or gaseous at normal ambient temperatures, such as most metals and gases like nitrogen, may also be measured in temperature ranges in which the material is liquid.

Figure 1:
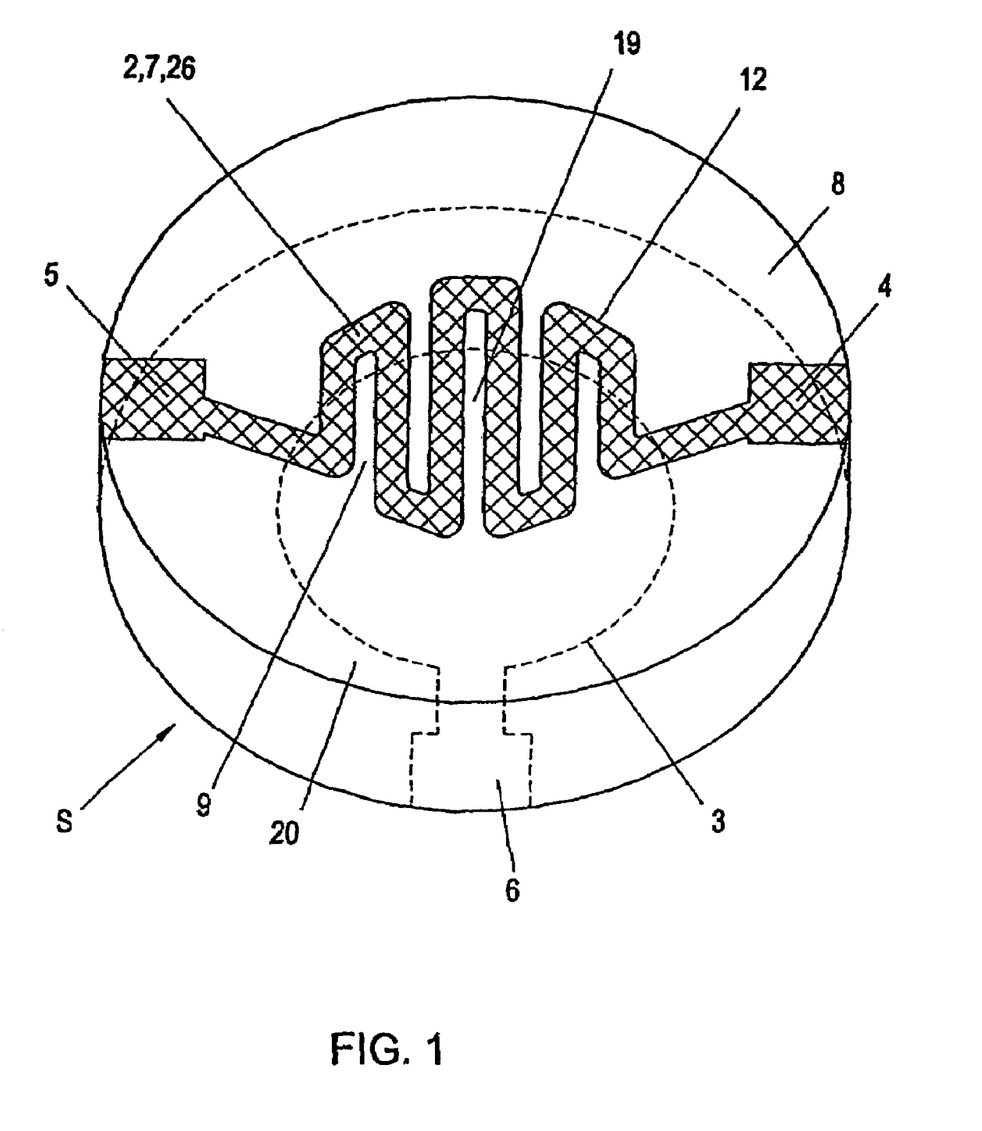
FIG. 1 shows an example embodiment of a sensor according to the present invention having a first embodiment of a heating electrode in an oblique view.
Figure 3:
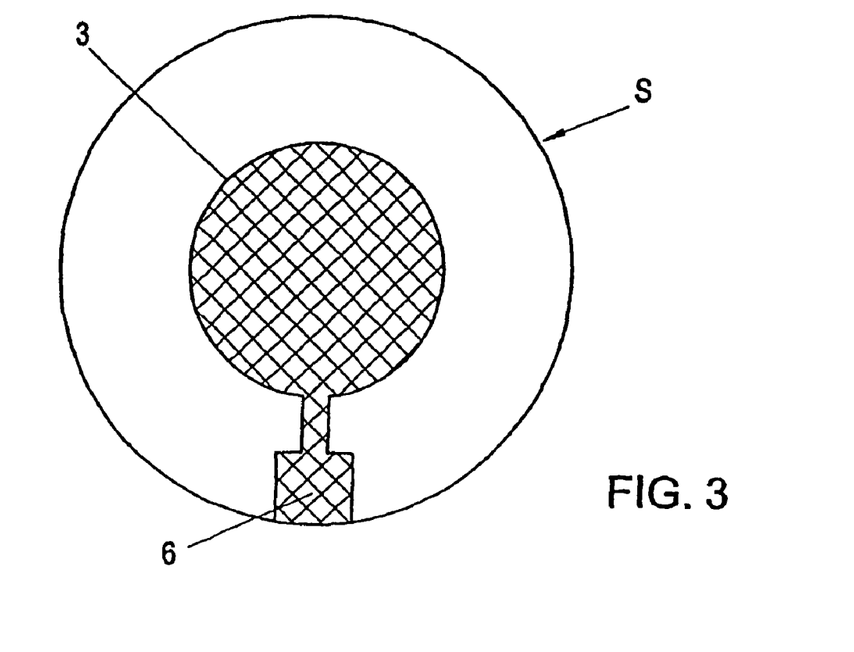
FIG. 3 shows a sensor according to FIG. 1 in a bottom view.
Figure 4:
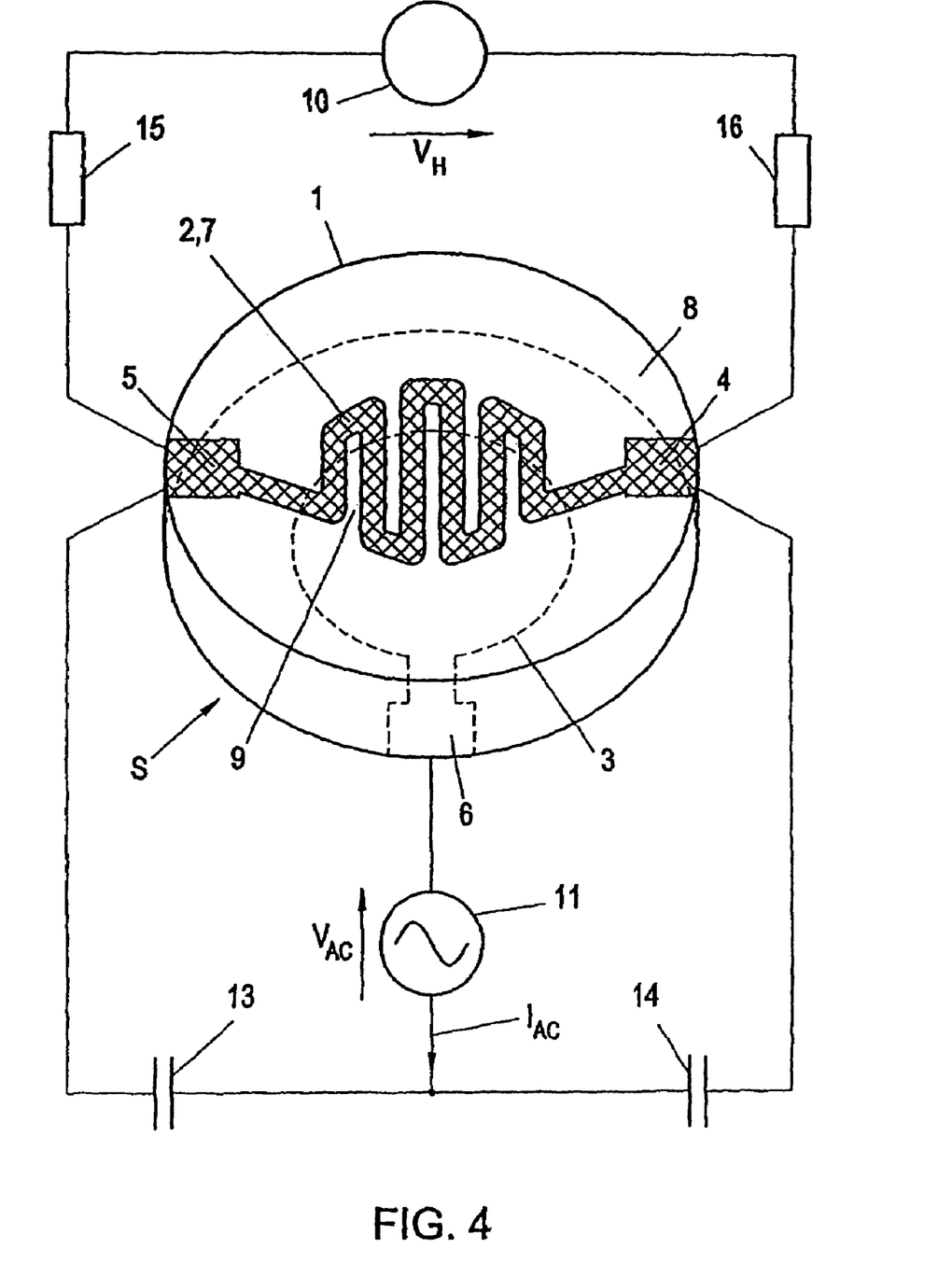
FIG. 4 schematically shows the control of a sensor according to FIG. 1.

FIG. 1 shows an oblique view of a first example embodiment of a sensor S according to the present invention. Sensor S, designed as a thickness shear oscillator, has a piezoelectric component 1, which is designed, in the first embodiment, as a circular platelet made of piezoelectric material (e.g., quartz having crystal orientation according to the known AT section). However, sensor S may also have other shapes according to the present invention, for example, a rectangular shape having different base surfaces such as a square or a rectangle. Conductive structures, for example, metal plating, are applied to both surfaces. A sensor S according to the present invention has at least one first starting electrode 7 and one second starting electrode 3, in addition to at least one heating electrode 2. In the embodiment, starting electrodes 3, 7 and heating electrode 2 are situated on or next to the at least one sensitive surface 8. The first embodiment of a sensor S according to the present invention, shown in FIG. 1, has a heating electrode 2, which is designed in one piece with the first starting electrode. The heating electrode has a meandering shape. However, as discussed below, heating electrode 2 may also have other shapes. Second starting electrode 3 is shown in FIG. 1 with simple dashed lines. FIG. 3 shows second starting electrode 3, which has a circular shape in the first embodiment of a sensor S. Second starting electrode 3 may also be designed in one piece with heating electrode 2. This may be advantageous when sensor S is fully surrounded by the liquid to be measured. Therefore, second starting electrode 3 may also have the shapes of heating electrode 2, independently of whether or not second starting electrode 3 and a heating electrode 2 are designed in one piece.

Starting electrodes 3, 7 and/or heating electrode 2 may include any conductive material, e.g., metals. Gold, chromium, copper, silver, rhodium, or aluminum are some of the metals for use in starting electrodes 3, 7. The above-named metals, as well as metals having a high resistivity such as manganese, titanium, or a resistor alloy according to DIN 17 471 are some of the metals for use in heating electrode 2.

Figure 2:
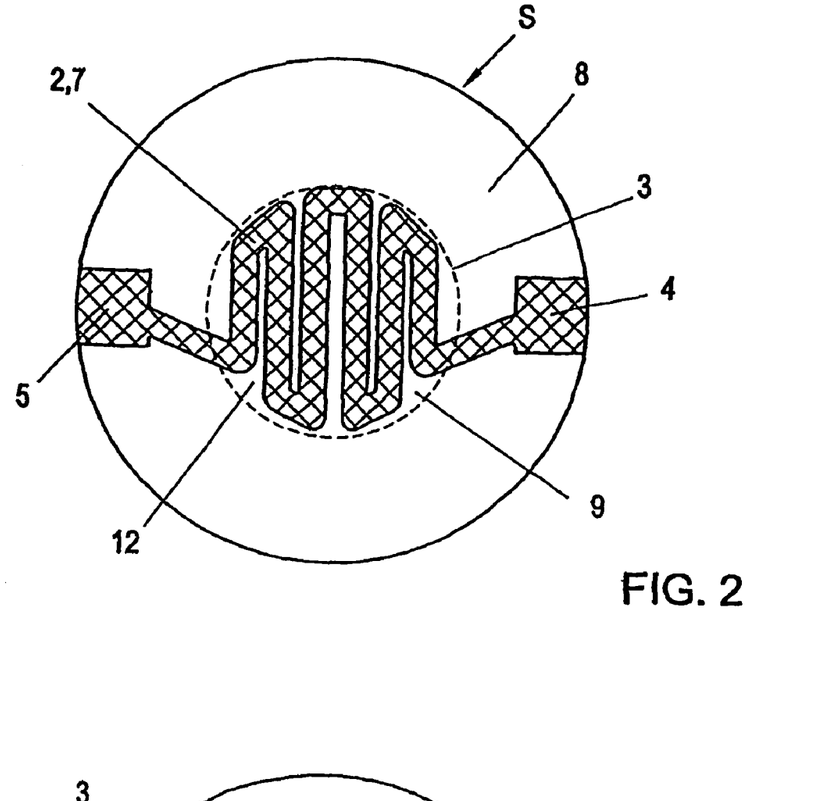
FIG. 2 shows a sensor according to FIG. 1 in a top view.

FIG. 2 shows the meandering shape of first starting electrode 7 and heating electrode 2, designed in one piece, according to the first embodiment.

Starting electrodes 3, 7 and heating electrode 2 are contacted via conductive contact surfaces 4, 5, 6. A heating voltage, e.g., a direct voltage $V_H$, is applied to terminals 4 and 5 for heating the structure. Corresponding surface 8 of the sensor is then heated. The liquid may be brought into contact either with both sensor surfaces or, optionally, just with the directly heated surface. In the first case, a measurement is not performed until after a waiting period when the entire sensor S has been heated.

An alternating voltage $V_{AC}$ is applied to heating electrode 2, i.e., first starting electrode 7 (i.e., terminals 4 and 5), as well as to second starting electrode 3 on the other side via terminal 6 for inducing mechanical oscillations. Heating electrode 2 functions, as described above, also as first starting electrode 7 for inducing acoustic oscillations. Capacitors 13, 14 and/or inductors 15, 16 (or resistors) may be used for isolating the heating current circuit from the alternating voltage circuit, as shown in an embodiment depicted in FIG. 4. The DC voltage for heating is supplied from a heating voltage source 10, via inductors 15, 16 (which may also be omitted) which are used for isolating source 10 from the applied alternating voltage. Alternating voltage 11 is supplied via capacitors 13, 14, which prevent a DC short-circuit of the heater winding. In this case, the impedance defined by the voltage $V_{AC}$ to current $I_{AC}$ ratio is used for detecting the viscosity, sensor S being operated in the range of the mechanical resonance frequency in the preferred embodiments. The depiction of the excitation via an alternating voltage source is to be understood in this context as schematic. The sensors may be inserted in circuits (e.g., oscillators or a control circuit) which are automatically set to the resonance frequency.

Figure 5:
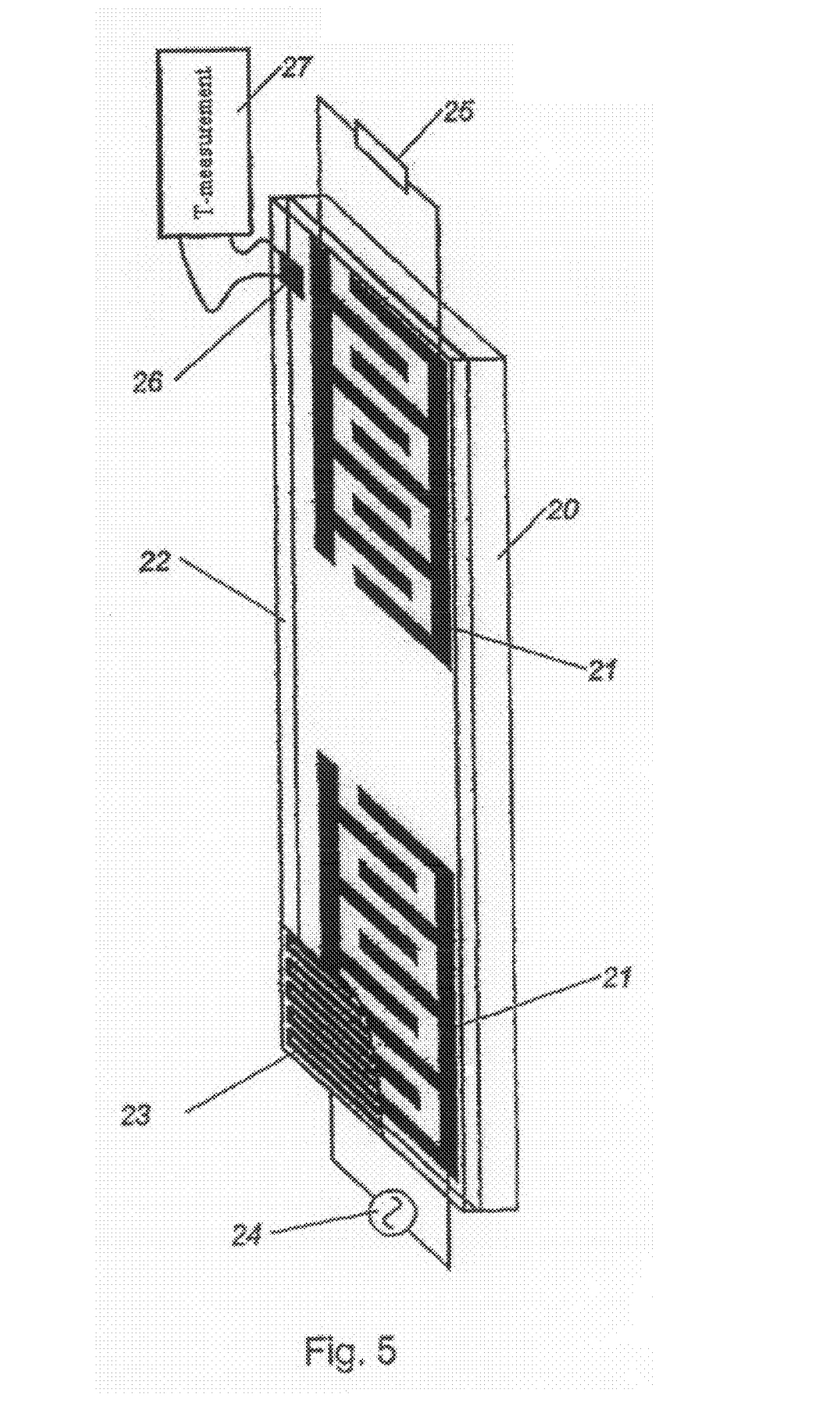
FIG. 5 shows a second example embodiment of a sensor according to the present invention having a second embodiment of a heating electrode in an oblique view.

FIG. 5 shows a second example embodiment of a sensor S according to the present invention as a delay line such as may be used in sensor applications in liquids; background explanations regarding the underlying component are found, for example, in B. Jakoby and M. J. Vellekoop, "Analysis and optimization of Love wave liquid sensors," IEEE Trans. on Ultrason., Ferroelec., and Freq. Contr., vol. 45: pp. 1293-1302, September 1998. In principle, the component is based on a piezoelectric substrate, for example, quartz 20, the crystal orientation being selected in such a way that shear waves may be electrically induced. The waves are induced via interdigital transducers 21, which are implemented by appropriate metal platings on the substrate. When the sensor is used as a delay line, one interdigital transducer is supplied by a source 24, while the other one is used as a receiver to which, for example, a consumer 25, e.g., a measuring instrument, is connected. Damping and delay (i.e., electrical phase) between input and output signal of this delay line thus defined may be electrically analyzed when used as sensor S. To guide the shear wave on the surface, a waveguide layer 22 (for example, silicon dioxide) may also be applied which, like an optical waveguide, guides the waves, which are known as "Love waves," bound to the surface. Due to this electrically insulating layer, an additional electrically conductive layer may also be applied to this waveguide layer to electrically shield the interdigital transducer against the liquid (this idea is described in more detail in the above-cited publication by Jakoby et al.). This shielding may be designed according to the present invention as heating electrode 2, for example, via conductive filaments 23 running close together, so that the shielding winding and heating electrode 2 may be functionally combined in the same layer.

The viscosity of liquids is highly temperature-dependent. Therefore, in the example embodiment of FIG. 5, a temperature sensor 26 may be integrated in sensor S and/or situated on the surface of sensor S. The temperature of the liquid or the surface temperature of sensor S may thus be detected directly on sensor S.

Since the penetration depth of the acoustic waves used for the measurement is very small, it is sufficient to heat the liquid to the predefinable temperature only in the area of sensor S. Due to the small amount of liquid that must be heated, it may be assumed that it is heated very quickly and that the surface temperature of sensor S is equal to the temperature of the liquid to be measured. In the example embodiments, temperature measuring sensor 26 may include the at least one heating electrode 2. Heating electrode 2 itself is then used for temperature measurement. The temperature may be measured, for example, by measuring the resistance of heating electrode 2 which changes with the temperature. However, any other type of temperature measurement 26 may also be provided such as with the help of a thermoelement.

FIGS. 6 through 9 show different example embodiments of heating electrode 2 of sensors S according to the present invention. It should be pointed out here that the present invention is not limited to the above-described embodiments of heating electrodes 2. Instead, any advantageous embodiment may be provided. The embodiments depicted in FIGS. 6 through 9 represent only a small sampling of the possible embodiments. FIGS. 6 through 9 only show the embodiment of heating electrode 2 of a sensor S. Other details of sensor S according to the present invention are not shown in FIGS. 6 through 9.

Heating electrode 2 spans a surface area 9. For example, in a meandering heating electrode 2, this surface area 9 is formed by the envelope of the outer turning points of the individual meanders. Generally speaking, surface area 9 is formed in such a way that it fully encloses heating electrode 2. Surface area 9 may have any desired shape. Heating electrode systems extending over a symmetric or partly symmetric surface area 9 are possible. Such a surface area 9 may have a central area 17, with a center 18, and in particular a center point 19. Depending on the specific shape of surface area 9, it will have a center point 19 or a central area 17. For the sake of simplicity, in the following we shall only refer to center 18.

Figure 8:
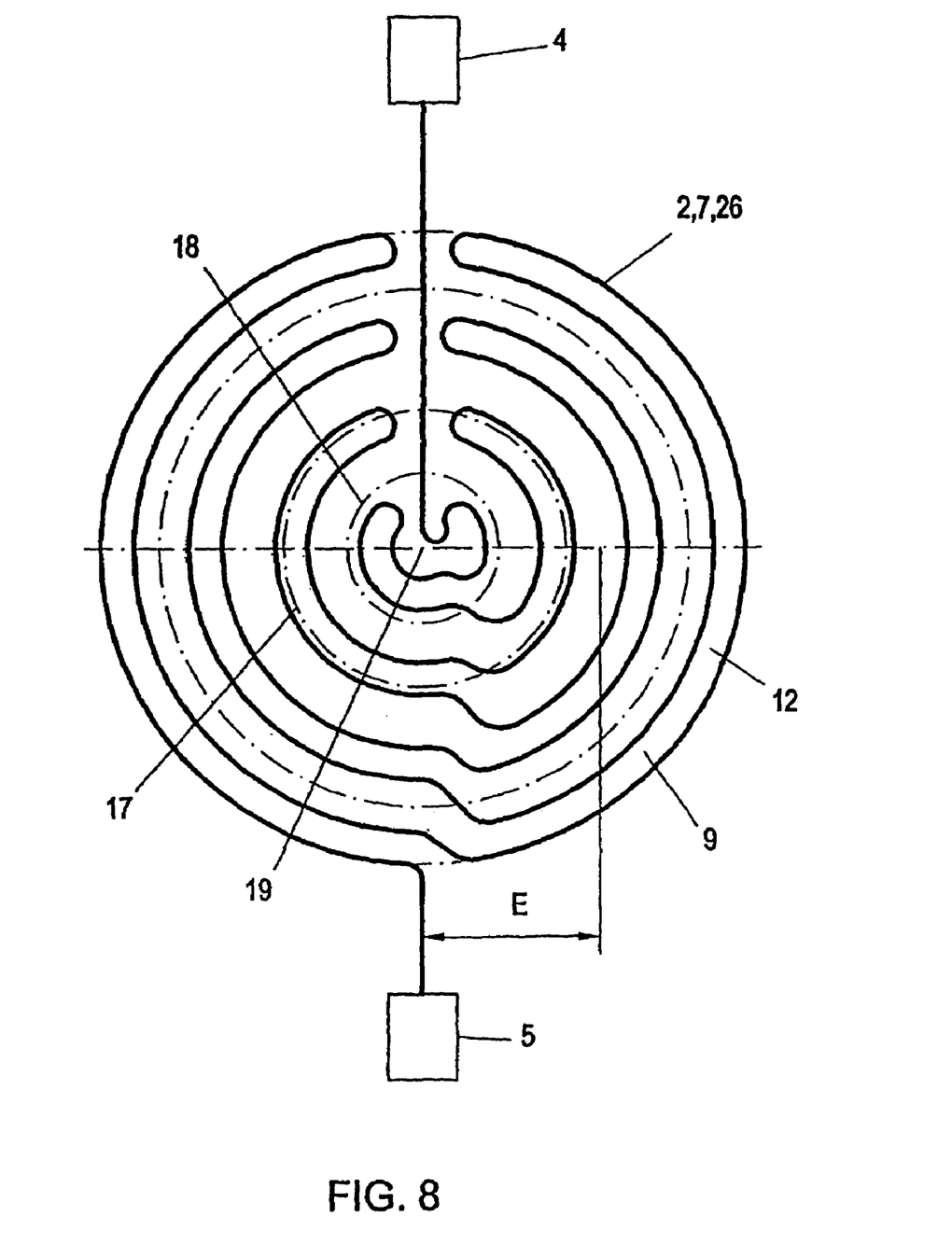
FIG. 8 shows a fifth embodiment of a heating electrode.

In the example embodiments of sensors S according to the present invention, the sensor may have an approximately uniform temperature distribution over surface area 9 in the operating temperature range. Uniformly heated surface areas 9 in particular have a non-uniform temperature distribution over surface area 9, central area 17 usually having a considerably higher temperature than edge area 12. Such a temperature distribution over heated surface area 9 results, in the case of a sensor S for viscosity measurements in liquids, in erroneous or less accurate results. To counteract this effect, in the example embodiments, edge area 12 is heated more intensively than central area 17 or the area around center 18. Therefore, in the example embodiments of sensors according to the present invention, the resistance per unit of length of the at least one heating electrode 2 may vary as a function of its distance E from central area 17, center 18, or center point 19, as shown in FIG. 8. As long as the accuracy of the ascertainable viscosity values is not necessary, the above-described embodiments may also be provided with a uniformly heated sensor S.

Heating electrode 2 is heated according to its resistance and thus according to the power dissipated across it. Therefore, heating electrode 2 may have at least two areas having different resistances per unit of length in order to heat certain areas of sensor S differently from other areas. The resistance of heating electrode 2 results from the resistivity of the material from which it is manufactured and from its cross-sectional area. Therefore, heating electrode 2 may have at least two areas of different cross sections; this cross-section change may be achieved by different widths of heating electrode 2 at a constant thickness, by different thicknesses of heating electrode 2 at a constant width, or by a combination of both options. In addition or independently, heating electrode 2 may have areas of different resistivities, i.e., areas made of different materials. Using these measures it may be achieved that individual areas of heating electrode 2 have a higher or lower temperature than other areas.

Figure 6:
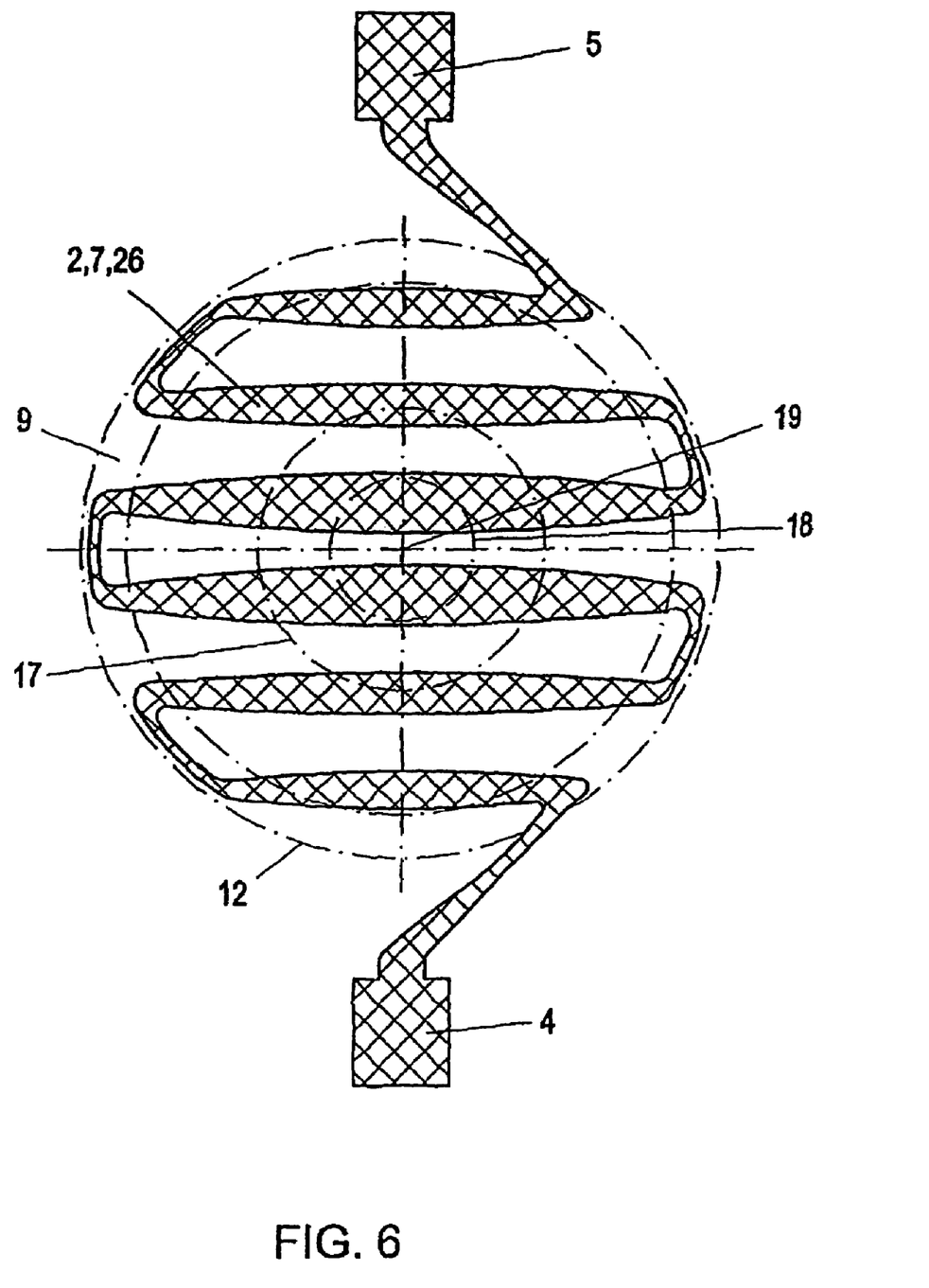
FIG. 6 shows a third embodiment of a heating electrode.

In the third embodiment of a heating electrode 2 according to FIG. 6, a meandering heating electrode 2 running over a circular surface area has a smaller width in areas situated farther away from center 18, i.e., at edge 12; therefore, at edge 12 heating electrode 2 has a higher resistance than at center 18; thus it heats edge 12 more intensively than center 18. A more homogeneous temperature distribution is thus established over the entire surface area 9 than in the case of a uniformly heated heating electrode 2.

Figure 7:
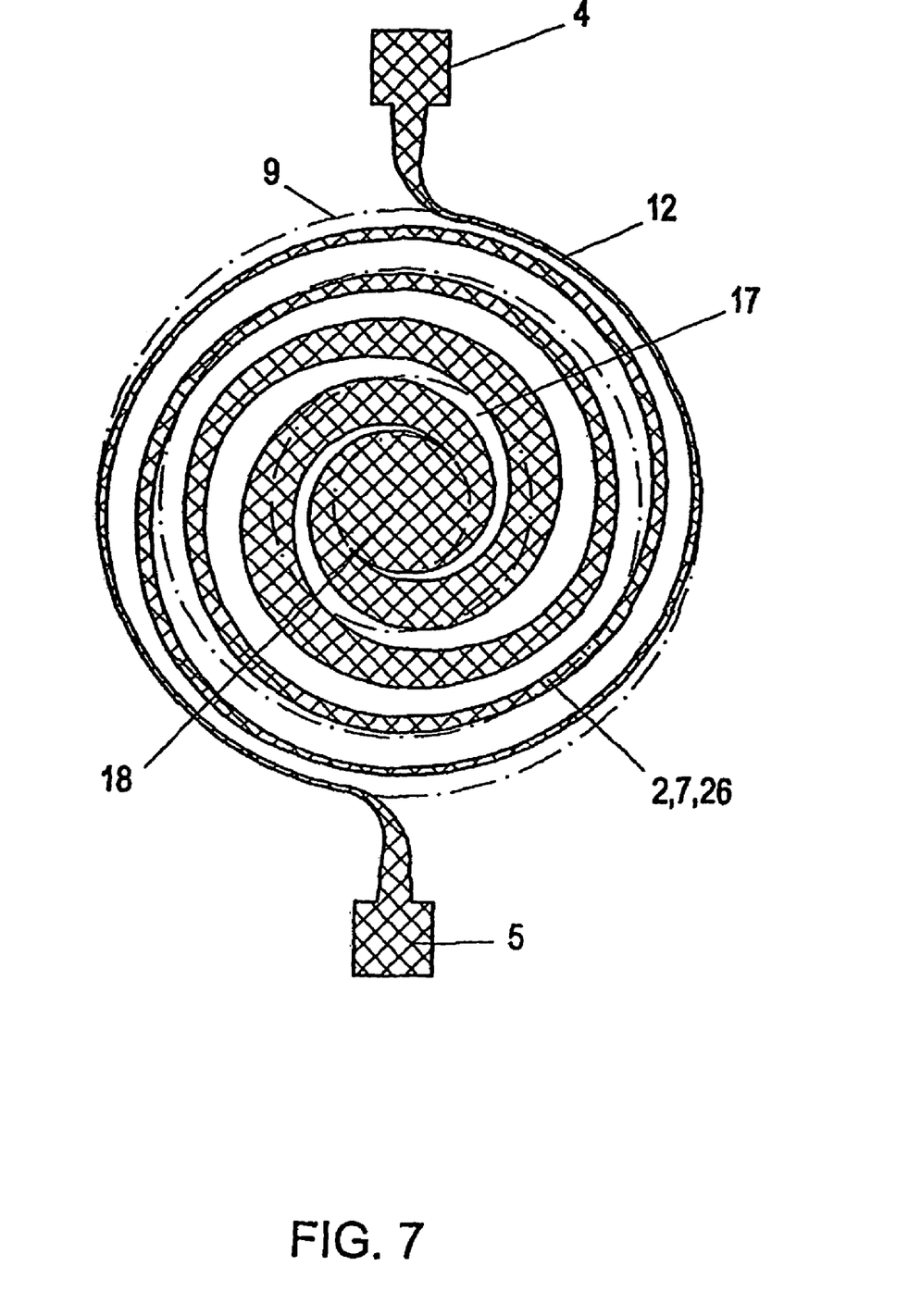
FIG. 7 shows a fourth embodiment of a heating electrode.

FIG. 7 shows a fourth embodiment of a meandering heating electrode 2 inscribed into a circular area 9. Heating electrode 2 has a helical shape and becomes wider toward center 18. As in the embodiment according to FIG. 6, this embodiment of heating electrode 2 also has an increased conductor cross section and thus a lower resistance per unit of length and a less intense heating of heating electrode 2 in center 18.

FIG. 8 shows a fifth embodiment of a meandering heating electrode 2 inscribed into a circular area 9. Heating electrode 2 is shown having a uniform width over its length. However, embodiments similar to those of FIG. 6 or 7 having varying widths may also be provided. A variation in resistance may be implemented in an embodiment according to FIG. 8, for example, and if planned with the aid of different thicknesses of heating electrode 2 or by a combination of materials having different resistivities.

Two adjacent heating electrodes 2 may also be arranged in such a way that, while the cross-section and material of a heating electrode 2 remain constant, a certain part of the area is more intensively heated than another part of the area. For example, the heating electrodes may lie closer together at edge 12 than at center 18.

Figure 9:
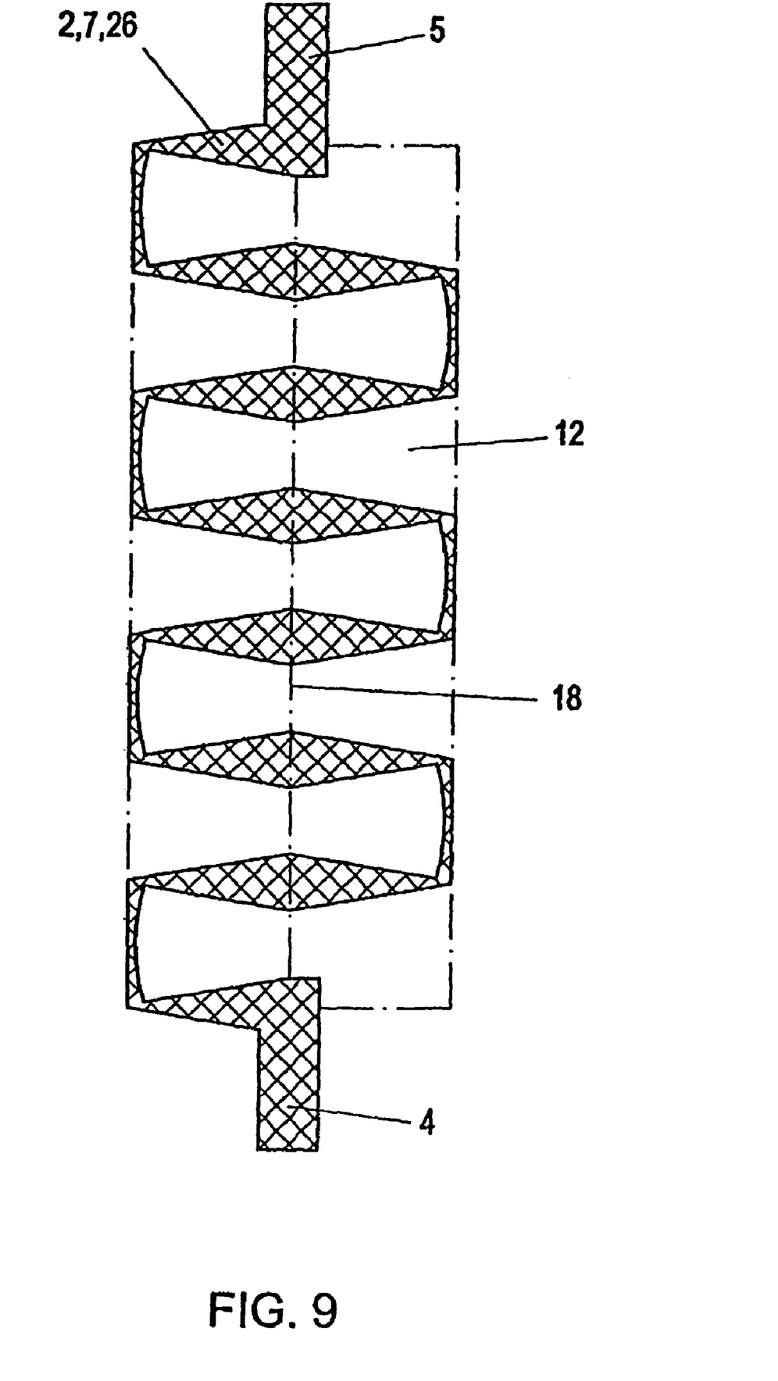
FIG. 9 shows a sixth embodiment of a heating electrode.

FIG. 9 shows a sixth embodiment of a heating electrode 2, heating electrode 2 spanning a rectangular area 9 and heating electrode 2 has different cross sections in different areas. As shown, the cross sections may diminish from center 18, which in this embodiment is formed by the center line, outward.

In particular, the example embodiments of heating electrode 2 according to the present invention depicted in FIGS. 6 through 9 are depictions of the idea and principle of the invention. They represent no limitation regarding the heating electrodes 2. In particular, the widths of heating electrodes 2, but also the distance between the individual areas of a heating electrode 2, are only depicted in principle and are in no way limiting.

In all the above-described embodiments of heating electrodes 2 according to the present invention, all possible and/or described options for varying the resistance per unit of length may be combined.

Alternatively to heating a heating electrode 2 differently in different areas, a plurality of different heating electrodes 2 may be provided, which may be arranged differently and each may be heated with a different intensity.

Additional devices for measuring the viscosity of liquids may be provided according to the present invention, in addition to a sensor S according to the present invention.

Furthermore, the present invention provides a method for measuring the viscosity of liquids in which at least one sensitive surface 8 of a sensor S is brought into contact with the liquid to be measured, sensor S being induced to oscillate by applying an alternating voltage, and a viscosity value of the liquid is ascertained from measured values of the electrical parameters, e.g., voltage and current, the liquid being heated by a heating electrode 2 in the area of sensitive surface 8.

Sensor S for viscosity measurement may be either fully immersed in the liquid or covered with the liquid only in the area of sensitive surface(s) 8. Heating electrode 2 is heated by applying an appropriate heating voltage, and in turn heats the surrounding liquid. The temperature of the liquid may be measured using a temperature sensor 26, which is may be integrated into sensor S.

In an example implementation of the method according to the present invention, it is possible to interrupt the heating of the liquid upon reaching a predefinable temperature, to measure the electrical parameters, and to ascertain the viscosity value of the liquid.

Since in many cases the viscosity value of the liquid is not only to be ascertained at a certain temperature, it may also be ascertained for a plurality of predefinable temperatures.

A curve of the liquid's viscosity plotted against the temperature may be formed from the individual viscosity values of the liquid at the predefinable temperatures.

A combination of some or all features of the above-described example embodiments of a sensor, a device and/or a method according to the present invention is within the scope of the present invention.

What is claimed is:

1. A sensor for measuring the viscosity of a liquid, comprising:
    at least one piezoelectric component configured as a resonator;
    at least one first starting electrode situated on a sensitive surface of the sensor;
    at least one second starting electrode; and
    at least one heating electrode provided for heating the liquid to be measured,
    wherein the at least one heating electrode is situated on or next to the sensitive surface of the sensor and is configured in one piece with the at least one first starting electrode,
    wherein the at least one heating electrode spans a surface area of the sensor having a central area,
    wherein the central area includes a center region, and the center region includes a center point,
    wherein the surface area of the sensor has an approximately uniform temperature distribution in an operating temperature range,
    wherein a resistance per unit of length of the at least one heating electrode varies for at least two areas of the at least one heating electrode, and
    wherein the resistance per unit of length of the at least one heating electrode varies as a function of distance from one of the central area, the center region, or the center point.

2. The sensor as recited in claim 1, wherein at least one of the at least one first starting electrode, the at least one second starting electrode, and the at least one heating electrode is coated with an insulation layer.

3. The sensor as recited in claim 1, wherein the at least one heating electrode has a meandering shape.

4. The sensor as recited in claim 1, wherein the at least one heating electrode has at least two areas of different cross sections.

5. The sensor as recited in claim 1, further comprising:
    a temperature measuring sensor.

6. The sensor as recited in claim 5, wherein the at least one heating electrode is incorporated in the temperature measuring sensor.

7. A sensor for measuring the viscosity of a liquid, comprising:
    at least one piezoelectric component configured as a resonator;
    at least one first starting electrode situated on a sensitive surface of the sensor;
    at least one second starting electrode; and
    at least one heating electrode provided for heating the liquid to be measured,
    wherein the at least one heating electrode is situated on or next to the sensitive surface of the sensor and is configured in one piece with the at least one first starting electrode,
    wherein the at least one heating electrode spans a surface area of the sensor having a central area,
    wherein the central area includes a center region, and the center region includes a center point,
    wherein the surface area of the sensor has an approximately uniform temperature distribution in an operating temperature range,
    wherein a resistance per unit of length of the at least one heating electrode varies for at least two areas of the at least one heating electrode, and
    wherein the resistance per unit of length of the at least one heating electrode increases with distance from one of the central area, the center region, or the center point, toward an edge of the surface area of the sensor.

8. The sensor as recited in claim 7, wherein the at least one heating electrode has a meandering shape.

9. The sensor as recited in claim 7, wherein the at least one heating electrode has at least two areas of different cross sections.

10. The sensor as recited in claim 7, further comprising:
    a temperature measuring sensor.

11. The sensor as recited in claim 7, wherein the at least one heating electrode is incorporated in the temperature measuring sensor.

12. The sensor as recited in claim 7, wherein at least one of the at least one first starting electrode, the at least one second starting electrode, and the at least one heating electrode is coated with an insulation layer.

13. The sensor as recited in claim 7, further comprising:
    a temperature measuring sensor, wherein the at least one heating electrode is incorporated in the temperature measuring sensor;
    wherein the at least one heating electrode has a meandering shape, wherein the at least one heating electrode has at least two areas of different cross sections, wherein the at least one heating electrode is incorporated in the temperature measuring sensor, and wherein at least one of the at least one first starting electrode, the at least one second starting electrode, and the at least one heating electrode is coated with an insulation layer.

* * * * *